United States Patent [19]

Camaggi et al.

[11] Patent Number: 5,334,605
[45] Date of Patent: Aug. 2, 1994

[54] THIAZOLYLPYRROLES HAVING A FUNGICIDAL ACTIVITY

[75] Inventors: Giovanni Camaggi, Novara; Lucio Filippini, San Donato Milanese; Marilena Gusmeroli, Nonza; Raul Riva, Novara; Carlo Garavaglia, Cuggiono; Luigi Mirenna, Milan; Luigi Mirenna, Milan, all of Italy

[73] Assignee: Ministero Dell'Universita' E Della Ricerca Scientifica E, Rome, Italy

[21] Appl. No.: 14,131

[22] Filed: Feb. 5, 1993

[30] Foreign Application Priority Data

Feb. 6, 1992 [IT] Italy .................. MI92A/000228

[51] Int. Cl.$^5$ .................. A01N 43/78; C07D 277/22
[52] U.S. Cl. .................. 514/365; 514/369; 548/182; 548/202
[58] Field of Search ........ 548/182, 202; 514/365, 514/369

[56] References Cited

U.S. PATENT DOCUMENTS 5,124,342  6/1992  Kerdesky et al. ............ 548/182

FOREIGN PATENT DOCUMENTS 0159677 10/1985  European Pat. Off. ........ 548/202
0411718  2/1991  European Pat. Off. ........ 548/202

OTHER PUBLICATIONS

CA 105(23) 209323p Synthesis . . . pyrrolidine sugar, Kini et al., p. 637, 1986.

*Primary Examiner*—Mary C. Lee
*Assistant Examiner*—Joseph K. McKane
*Attorney, Agent, or Firm*—Rogers & Wells

[57] ABSTRACT

Compounds based on 2-thiazole-2-ylpyrrole, with a fungicidal activity, having the general formula (I):

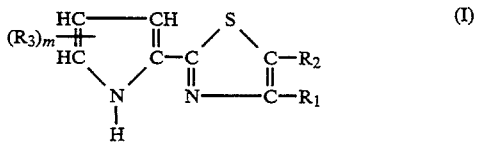

13 Claims, No Drawings

THIAZOLYLPYRROLES HAVING A FUNGICIDAL ACTIVITY

The present invention relates to compounds based on 2-thiazol-2-ylpyrroles.

More specifically, the present invention relates to compounds based on 2-thiazol-2-ylpyrroles having a high antifungal activity, a procedure for their preparation and their use in the agricultural field as fungicides.

The present invention consequently relates to compounds based on 2-thiazol-2-ylpyrrole having the general formula (I):

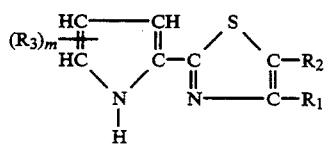

wherein:
- $R_1$ represents a hydrogen atom, a $C_1$–$C_6$ alkyl group either linear or branched, a phenyl group, a $C_1$–$C_4$ alkoxyl group, a phenoxyl group, a $C_4$–$C_6$-heterocycloxylic group, optionally substituted with halogens, such as chlorine, bromine, iodine, or with $C_1$–$C_4$ alkyl radicals;
- $R_2$ represents a hydrogen atom, or a $C_1$–$C_6$ alkyl or haloalkyl group, either linear or branched;
- $R_3$ represents a $C_1$–$C_6$ alkyl or haloalkyl group, either linear or branched;
- m is an integer between 0 and 4.

The products having general formula (I) are antifungal agents for agricultural purposes.

Examples of $R_1$ radicals are: methyl, isopropyl, ter-butyl, trifluoromethyl, perfluorobutyl, methoxyl, ethoxyl, trifluoromethoxyl, 1,1,2,2-tetrafluoroethoxyl, phenyl, 4-chlorophenyl, 2,4-dichlorophenyl, 3,4-dichlorophenyl, 2,4,6-trichlorophenyl, 3-trifluoromethylphenyl, 4-trifluoromethylphenyl, 4-fluorophenyl, 2,4dichlorophenyl, 4-chlorophenoxyl, 2,4-dichlorophenoxyl, 2,4,6-trichlorophenoxyl, 3,5-dichloropyridoxy-2-yl, 5-trifluoromethylpyridoxy-2-yl, etc.

Examples of R2 and R3 radicals are: methyl, ethyl, isopropyl, ter-butyl, 2,2-dimethylbutyl, trifluoromethyl, 1,1,2,2-tetrafluoroethyl, etc.

Compounds having general formula (I) not illustrated in the examples, but equally interesting for their fungicidal activity are: [4-(2,4-dichlorophenyl) thiazol-2-yl]pyrrole, [4-(isopropyl)thiazol-2yl]pyrrole, [4-(trifluoromethyl)thiazol-2-yl]pyrrole, [4-(trifluoromethoxy)thiazol-2-yl]pyrrole, [4-(1,1,2,2 tetrafluoroethoxy)-thiazol-2-yl]pyrrole, [4-(3-tri-fluoromethylphenyl)-thiazol-2-yl]pyrrole, [4-(4-tr fluoromethylphenyl ) thiazol- 2-yl ]pyrrole, [4-(2,4dichlorophenoxy) thiazo -2-y]pyrrole, [4-(2,4,6-trichlorophenoxy)thiazol-2-yl]pyrrole, [4-(5-trifluoromethylpyridoxy-2-yl) thiazol-2-yl ]pyrrole, etc.

A procedure for obtaining the compounds of the present invention, includes reacting pyrroles having general formula (II):

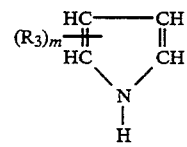

wherein $R_3$ has the meaning defined above, with ethoxycarbonylisothiocyanate (III):

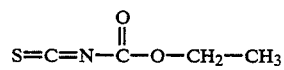

in a chlorinated solvent, such as for example dichloroethane or dichloromethane, or in an alcoholic solvent, such as for example methanol or ethanol, at a temperature ranging from 0° C. to the boiling point of the solvent, thus obtaining the pyrrole-thioamide having general formula (IV):

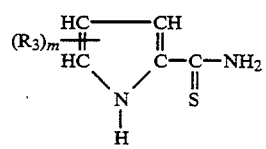

wherefrom, by reaction with an α-bromoketone having general formula (V):

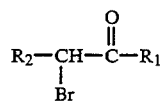

wherein $R_1$ and $R_2$ have the same meaning described above, in an alcoholic solvent, such as methanol or ethanol, or in a dipolar aprotic solvent, such as dimethylformamide or N-methylpyrrolidone, at a temperature ranging from room temperature to the boiling point of the solvent, the compound having general formula (I) is obtained.

The compounds of the present invention may also be obtained with another procedure which includes reacting the zinc salt of pyrrole having general formula (II) with a 2-bromothiazole having general formula (VI):

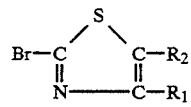

wherein $R_1$ and $R_2$ have the same meaning described above, in the presence of a salt of palladium, such as for example palladium chloride, and of a phosphine, such as triphenylphosphine or triorthotolylphosphine, in a dipolar-aprotic solvent, such as N-methylpyrrolidone, or in an aromatic solvent, such as toluene or xylene, at a temperature ranging from 100° C to the reflux temperature of the solvent.

The compounds having general formula (I) have a particularly high fungicidal activity against phytopathogen fungi which attack cultivations of vines, cereals, Cocurbitacee and fruit trees.

They have both a preventive and curative activity when applied to useful plants or their parts, such as leaves, and are particularly effective in preventing diseases caused by obligate pathogenic fungi, such as, for example those belonging to the species Erysiphe and Helminthosporium.

Plant diseases which can be fought with the compounds of the present invention are, for example, the following:

Helminthosporium of cereals;
*Plasmopara viticola* of vines;
Phytium of horticultural products;
*Sphaerotheca fuliginea* of cocurbitacee (e.g. cucumbers);
Septoria of cereals;
*Ervsiphe graminis* of cereals;
Rhynchosporium of cereals;
*Podosphaera leucotricha* of apple-trees;
*Uncinula necator* of vines;
*Venturia inequalis* of apple-trees;
*Piricularia oryzae* of rice;
Botrytis cinerea;
Fusarium of cereals; etc.

The compounds having general formula (I), as well as carrying out both a curative and preventive fungicidal action as described above, also have a limited or nonexistent phytotoxicity.

For the practical uses of agriculture it is often useful to have fungicidal compositions containing one or more of the compounds having general formula (I), possibly also in an isomeric form, as active substance.

These compositions may be applied on any part of the plant, for example, leaves, stems, branches and roots, or on the seeds, before sowing, or even on the soil where the plant grows.

Compositions can be used in the form of dry powders, wettable powders, emulsionable concentrates, micro-emulsions, pastes, granules, solutions, suspensions, etc.: the choice of the type of composition depends on the specific use.

The compositions are prepared using the known methods, for example by diluting or dissolving the active substance with a solvent medium and/or solid diluent, possibly in the presence of surface-active agents.

Solid diluents, or supports, which can be used are: silica, kaolin, bentonitc, talc, infusorial earth, dolomite, calcium carbonate, magnesia, chalk, clays, synthetic silicates, attapulgite, sepiolite.

As liquid diluents, as well as water naturally, it is possible to use various types of solvents, for example aromatic solvents (xylols or mixtures of alkylbenzols), chloro aromatics (chlorobenzol), paraffins (fractions of petroleum), alcohols (methanol, propanol, butanol, octanol), amines, amides (N,N'-dimethylformamide, N-methylpyrrolidone), ketones (acetone, cyclohexanone, acetophenone, isophorone, ethylamylketone), esters (isobutyl acetate).

Surface-active agents which can be use are the salts of sodium, calcium or of triethanolamine of alkylsulphates, alkylsulphonates, alkylarylsulphonates, polyethoxylated alkylphenols, fat alcohols condensed with ethylene oxide, polyoxyethylated fat acids, polyoxyethylated esters of sorbitol, ligninsulphonates.

The compositions may also contain special additives for particular purposes, such as for example adhering agents such as arabic rubber, polyvinyl alcohol, polyvinylpyrrolidone.

If desired it is also possible to add other compatible active substances to the compositions of the present invention, such as fungicides, phytoregulators, antibiotics, weed-killers, insecticides, fertilizers.

The concentration of active substance in the above compositions can vary within a wide range, depending on the active compound, cultivation, pathogen, environmental conditions and type of formulation used.

In general the concentration of active substance varies from 0.1 to 95%, preferably from 0.5 to 90%.

The following examples provide an illustration of the present invention but do not limit it in any way.

EXAMPLE 1

Preparation of [4-(4-chlorophenyl)thiazol-2-yl]pyrrole (Compound No. 1)

5.0 g of pyrrole-2-thioamide are dissolved in 15 cm$^3$ of anhydrous ethanol, in a nitrogen atmosphere.

9.3 g of 4-chlorophenacylbromide are then added and the mixture is heated to reflux temperature for three hours.

The solution thus obtained is diluted with 30 cm$^3$ of 2N aqueous sodium carbonate and is extracted with ethyl acetate.

The solution is subsequently concentrated at reduced pressure and the crude product obtained is purified on silica gel, using hexane:ethyl acetate in a ratio of 7:3 as eluant.

9.8 g of compound No.1 are obtained with a yield of 94.8%, the structure of which is shown in table 1.

Table 2 shows the NMR spectroscopy data.

EXAMPLE 2

Preparation of (4-terbutylthiazol-2-yl)pyrrole (Compound No. 3)

5.0 g of pyrrole-2-thioamide are dissolved in 12 cm$^3$ of anhydrous ethanol, in a nitrogen atmosphere.

6.8 g of 1-bromo-3,3-dimethylbutan-2-one are then added and the mixture is heated to reflux temperature for four hours.

The solution thus obtained is diluted with 35 cm$^3$ of 2N aqueous sodium carbonate and is extracted with ethyl acetate.

The solution is subsequently concentrated at reduced pressure and the crude product obtained is purified on silica gel, using hexane:ethyl acetate in a ratio of 7:3 as eluant.

5.7 g of compound No.3 are obtained with a yield of 51.3%, the structure of which is shown in table 1.

Table 2 shows the NMR spectroscopy data.

EXAMPLES 3-7

Using the same procedure described in example 1, compounds No. 2 and 4-7 were prepared, whose structure is shown in table 1.

The relative NMR spectroscopy data are shown in table 2.

EXAMPLE 8

Determination of the Preventive Fungicidal Activity against *Helminthosporim teres*

Leaves of barley cultivar Arna, grown in vases in a conditioned environment, are sprayed on both sides with compounds No. 1-7 in a 20% by volume hydroacetonic solution of acetone (the concentration of fungicide is 200 ppm).

After remaining two days in a conditioned environment at 20° C. and 70% relative humidity, the plants were sprayed on both sides of the leaves with an aqueous suspension of conidia of *Helminthosporium teres* (250000 conidia per cm$^3$).

After remaining 24 hours in an environment saturated with humidity at 21° C., the plants were kept in a conditioned environment to allow for the incubation of the fungus.

At the end of this period (12 days), complete control of the disease was obtained.

TABLE 1

| Compound | $R^2$ | $R^3$ | $R^1$ |
|---|---|---|---|
| 1 | H | H | 4-chlorophenyl |
| 2 | H | H | phenyl |
| 3 | H | H | t-butyl |
| 4 | H | H | methyl |
| 5 | H | H | cyclopropyl |
| 6 | CH$_3$ | H | t-butyl |
| 7 | CH$_3$ | Rf | t-butyl |

Rf = perfluorohexyl

TABLE 2

| Compound | NMR 60MHz spectroscopy data (DMSO-D$^6$) |
|---|---|
| 1 | 6.1(m, 1H), 6.7(m, 2H), 7.1(s, 1H), 7.2(m, 2H), 7.8(m, 2H), 9.7(s, 1H). |
| 2 | 6.1(m, 1H), 6.6(m, 2H), 7.3(m, 3H), 7.8(m, 2H), 9.8(s, 1H). |
| 3 | 1.3(s, 9H), 6.2(m, 1H), 6.6(m, 1H), 6.7(s, 1H), 6.8(m, 1H), 9.8(s, 1H). |
| 4 | 2.4(d, 3H), 6.2(m, 1H), 6.7(m, 1H), 6.8(m, 1H), 9.8(m, 1H). |
| 5 | 0.9(m, 4H), 2.1(m, 1H), 6.3(m, 3H), 6.6(m, 1H), 6.7(m, 1H), 6.8(m, 1H), 10.2(s, 1H). |
| 6 | 1.4(s, 9H), 2.4(s, 3H), 6.1(m, 1H), 6.4(m, 1H), 6.6(m, 1H), 9.7(s, 1H). |
| 7 | 1.6(s, 9H), 2.7(s, 3H), 6.8(m, 1H), 7.4(m, 1H), 10.7(s, 1H). |

We claim:

1. Compounds based on 2-thiazol-2-ylpyrrole having the general formula ( I ):

$$\text{(R}_3\text{)}_m \begin{array}{c} HC\text{---}CH \\ \| \quad \| \\ HC \quad C\text{---}C \\ \diagdown N \diagup \| \quad \| \\ | \quad N\text{---}C\text{---}R_1 \\ H \end{array} \begin{array}{c} S \\ \diagup \diagdown \\ C\text{---}R_2 \end{array} \quad (I)$$

wherein:
R$_1$ represents a hydrogen atom, a C$_1$–C$_6$ alkyl group either linear or branched, a phenyl group, a C$_1$–C$_4$ alkoxyl group, a phenoxyl group, a C$_4$–C$_6$ heterocycloxylic group, optionally substituted with halogens, such as chlorine, bromine, iodine, or with C$_1$–C$_4$ alkyl radicals;
R$_2$ represents a hydrogen atom, or a C$_1$–C$_6$ alkyl or haloalkyl group, either linear or branched;
R$_3$ represents a C$_1$–C$_6$ alkyl or haloalkyl group, either linear or branched;
m is an integer between 0 and 4.

2. Antifungal agents for agricultural purposes composed of compounds based on 2-thiazol-2ylpyrrole having general formula (I):

$$\text{(R}_3\text{)}_m \begin{array}{c} HC\text{---}CH \\ \| \quad \| \\ HC \quad C\text{---}C \\ \diagdown N \diagup \| \quad \| \\ | \quad N\text{---}C\text{---}R_1 \\ H \end{array} \begin{array}{c} S \\ \diagup \diagdown \\ C\text{---}R_2 \end{array} \quad (I)$$

wherein:
R$_1$ represents a hydrogen atom, a C$_1$–C$_6$ alkyl group either linear or branched, a phenyl group, a C$_1$–C$_4$ alkoxyl group, a phenxoyl group, a C$_4$–C$_6$ heterocycloxylic group, optionally substituted with halogens, such as chlorine, bromine, iodine, or with C$_1$–C$_4$ alkyl radicals;
R$_2$ represents a hydrogen atom, or a C$_1$–C$_6$ alkyl or haloalkyl group, either linear or branched;
R$_3$ represents a C$_1$–C$_6$ alkyl or haloalkyl group, either linear or branched;
m is an integer between 0 and 4.

3. Antifungal agents for agriculture purposes according to claim 2, wherein R$_1$ is: methyl, isopropyl, terbutyl, trifluoromethyl, perfluorobutyl, methoxyl, ethoxyl, trifluoromethoxyl, 1,1,2,2-tetrafluoroethoxyl, phenyl, 4-chlorophenyl, 2,4-dichlorophenyl, 3,4-dichlorophenyl, 2,4,5-trichlorophenyl, 3-trifluoromethylphenyl, 4-trifluoromethylphenyl, 4-fluorophenyl, 2,4-dichlorophenyl, 4-chlorophenoxyl, 2,4-dichlorophenoxyl, 2,4,6-trichlorophenoxyl, 3,5-dichloropyridoxy-2-yl, 5-trifluoromethylpyridoxy-2-yl.

4. Antifungal agents for agriculture purposes according to claim 2, wherein R$_2$ and R$_3$ are: methyl, ethyl, isopropyl, ter-butyl, 2,2-dimethylbutyl, trifluoromethyl, 1,1,2,2-tetrafluoroethyl.

5. Antifungal agent for agriculture purposes according to claim 2, composed of [4- ( 4-chlorophenyl thiazol-2-yl ]pyrrole.

6. Antifungal agent for agricultural purposes according to claim 2, composed of ( 4-phenyl-thiazol-2-yl) pyrrole.

7. Antifungal agent for agricultural purposes according to claim 2, composed of (4-terbutylthiazol-2-yl) pyrrole.

8. Antifungal agent for agricultural purposes according to claim 2, composed of (4-methylthiazol-2-yl) pyrrole.

9. Antifungal agent for agricultural purposes according to claim 2, composed of (4-cyclopropylthiazol-2-yl) pyrrole).

10. Antifungal agent for agricultural purposes according to claim 2, composed of ( 4-terbutyl-5-methyl-thiazol-2-yl ) pyrrole.

11. Antifungal agent for agricultural purposes according to claim 2, composed of (4-terbutyl-5-methyl-thiazol-2-yl)-6-perfluorohexylpyrrole.

12. Fungicidal compositions containing one or more of the compounds of claim 2 either alone or in the presence of solid supports, liquid diluents, surface-active agents or other active principles.

13. Method for fighting fungal infections consisting in applying the fungicidal compositions according to claim 12 on plants, leaves, stems, branches and roots, or on the seeds before sowing, or on the soil where the plant grows.

* * * * *

UNITED STATES PATENT AND TRADEMARK OFFICE
CERTIFICATE OF CORRECTION

PATENT NO. : 5,334,605
DATED : August 2, 1994
INVENTOR(S) : Giovanni Camaggi et al It is certified that error appears in the above-indentified patent and that said Letters Patent is hereby corrected as shown below:

On the cover page of the patent, under the heading "[75] Inventors:", it should read as --Giovanni Camaggi; Lucio Filippini; Marilena Gusmeroli; Raul Riva; Giampaolo Zanardi; Carlo Garavaglia; and Luigi Mirenna--.

In column 6: In Claim 3, in line 6, "2,4,5-trichlorophenyl" should read as --2,4,6-trichlorophenyl--;

In column 6: In Claim 3, in line 9, "2,4,6-trichlo-phenoxyl" should read as --2,4,6-trichlorophenoxyl--;

In column 6: In Claim 4, in line 1, the word "agriculture" should read as --agricultural--; and In column 6: In Claim 5, in line 1, the word "agriculture" should read as --agricultural--.

Signed and Sealed this

Fifteenth Day of November, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,334,605
DATED : August 2, 1994
INVENTOR(S) : Giovanni Camaggi, et. al.

It is certified that error appears in the above-indentified patent and that said Letters Patent is hereby corrected as shown below:

Title page, item [73], Assignee: should read --Ministero Dell' Universita' E Della Ricerca Scientifica E Tecnologica--;

Signed and Sealed this

Eighteenth Day of April, 1995

Attest:

BRUCE LEHMAN

Attesting Officer

*Commissioner of Patents and Trademarks*